United States Patent [19]

Bartoldus et al.

[11] 4,258,210
[45] Mar. 24, 1981

[54] PROCESS FOR MANUFACTURING SODIUM PANTOTHENATE

[75] Inventors: Dieter Bartoldus, Riehen; Emil Broger, Magden, both of Switzerland

[73] Assignee: Hoffmann-La Roche Inc., Nutley, N.J.

[21] Appl. No.: 37,166

[22] Filed: May 8, 1979

[30] Foreign Application Priority Data

May 18, 1978 [CH] Switzerland .................. 5387/78

[51] Int. Cl.³ .................... C07C 102/06; C07C 99/10
[52] U.S. Cl. ........................ 562/569; 562/576
[58] Field of Search .................... 562/576, 569

[56] References Cited

U.S. PATENT DOCUMENTS

| | | | |
|---|---|---|---|
| 2,335,605 | 11/1943 | Paden | 562/576 |
| 2,335,997 | 12/1943 | Carlson | 562/576 |
| 2,336,067 | 12/1943 | Carlson | 562/576 |
| 2,367,791 | 1/1945 | Parke | 562/569 |
| 2,418,902 | 4/1947 | Rogers | 562/569 |
| 2,441,949 | 5/1948 | Badcock | 562/569 |
| 2,442,143 | 5/1948 | Pickel | 562/569 |
| 2,819,303 | 1/1958 | Griffith | 562/576 |
| 2,845,456 | 7/1958 | Kagan | 562/569 |
| 2,956,080 | 10/1960 | Beutel | 562/576 |
| 3,150,175 | 9/1964 | Griffith | 562/569 |
| 3,935,256 | 1/1976 | Verbeeck | 562/576 |
| 4,052,451 | 10/1977 | Lekberg | 562/576 |

FOREIGN PATENT DOCUMENTS

| | | | |
|---|---|---|---|
| 117147 | 7/1943 | Australia | 562/569 |
| 117846 | 12/1943 | Australia | 562/569 |
| 529156 | 8/1956 | Canada | 562/569 |
| 573457 | 4/1959 | Canada | 562/569 |
| 632472 | 12/1961 | Canada | 562/569 |
| 49-13115 | 5/1974 | Japan | 562/576 |
| 49-47313 | 5/1974 | Japan | 562/576 |
| 49-110626 | 10/1974 | Japan | 562/576 |
| 551883 | 3/1943 | United Kingdom . | |
| 552641 | 4/1943 | United Kingdom | 562/569 |
| 553317 | 5/1943 | United Kingdom . | |
| 557761 | 12/1943 | United Kingdom | 562/569 |
| 558494 | 1/1944 | United Kingdom | 562/576 |
| 660722 | 11/1951 | United Kingdom . | |

OTHER PUBLICATIONS

Russu, Chem. Abst., 80:108,851u (1974).
Gora–Tsermegas, Chem. Abst., 86:139357r (1977).
Ford, J. Am. Chem. Soc., 67, pp. 876–877 (1945).
Ford, Org. Syn. 27, pp. 1–3 (1947).

Primary Examiner—Natalie Trousof
Assistant Examiner—Michael Shippen
Attorney, Agent, or Firm—Jon S. Saxe; Bernard S. Leon; George W. Johnston

[57] ABSTRACT

A process for producing sodium pantothenate from $\beta$-aminopropionitrile is disclosed.

14 Claims, No Drawings

PROCESS FOR MANUFACTURING SODIUM PANTOTHENATE

BACKGROUND OF THE INVENTION

1. Field of the Invention

The present invention is concerned with a process for the manufacture of a salt, namely, sodium pantothenate.

2. Description of the Prior Art

In a prior art process, sodium D or DL-pantothenate was obtained by reacting relatively dry sodium alaninate with L or DL-pantolactone, respectively.

The sodium alaninate for this known process was prepared and dried by a complex circuitous procedure. To obtain the dried sodium alaninate, β-amino-propionitrile was saponified with caustic soda and the resulting sodium alaninate was hydrolyzed to give β-alanine. By drying and then reacting the dried β-alanine with sodium methylate, one obtained the desired dry sodium alaninate. The prior art procedure for producing dry sodium alaninate apparently theorized that a dry sodium alaninate suitable for reaction with pantolactone can be obtained only by the above-described roundabout route using β-alanine.

We have discovered a process for producing sodium pantothenate from sodium alaninate which avoids the circuitous prior art procedure for producing dry sodium alaninate via β-alanine.

SUMMARY OF THE INVENTION

The present invention concerns a process for producing sodium L or DL-pantothenate.

In accordance with this invention, β-aminopropionitrile is saponified with aqueous caustic soda to yield sodium alaninate. The resulting sodium alaninate is dried to a water content of at most about 1% by weight and dissolved in a solvent. The resulting solution is reacted with L or DL-pantolactone to produce sodium D or DL-pantothenate.

Sodium D-pantothenate is useful in the treatment of vitamin $B_5$ (pantothenic acid) deficiencies.

DETAILED DESCRIPTION OF THE INVENTION

The present invention concerns a process for producing sodium D or DL-pantothenate from β-aminopropionitrile via dry sodium alaninate. It has been found that sodium pantothenate can be obtained in a simple manner by saponifying β-aminopropionitrile with aqueous caustic soda to give sodium alaninate and reacting this directly—after drying to a water content of at most 1% by weight and dissolution in a solvent—with pantolactone to give sodium pantothenate.

Sodium D-pantothenate is useful for treating vitamin $B_5$ (pantothenic acid) deficiencies.

As used herein, caustic soda comprises sodium hydroxide. Lower alkyl means alkyl groups having from 1 to 7 carbon atoms (e.g. methyl, ethyl n-propyl, isopropyl and hexyl). Lower alkanol connotes alkanols having 1-7 carbon atoms (e.g. methanol, isopropanol and hexanol). One bar equals 0.987 atmosphere.

In accordance with the present invention, any conventional technique or procedure for saponifying β-aminopropionitrile with aqueous caustic soda may be utilized. For example, the saponification of β-aminopropionitrile with aqueous caustic soda can be carried out batch-wide or continuously. When the saponification is carried out batch-wise, it is preferred to add the β-aminopropionitrile slowly to the aqueous caustic soda.

The saponification can be carried out at atmospheric pressure or at higher pressures (e.g. 0–6 bar), at temperatures of about 100° to about 130° C. and at corresponding residence times of about 0.5 to about 4 hours. An excess of aqueous caustic soda (e.g. about 103 to about 110 mole percent) may be utilized in the saponification. The excess aqueous caustic soda then can be neutralized by any conventional techniques. A suitable procedure includes adding β-alanine after the saponification has been carried out.

In carrying out the process of the present invention, it is preferred to dry the sodium alaninate to a water content of 0.3 to about 1% by weight, preferably at most about 0.5% by weight.

With the invention, the sodium alaninate is dried to the desired water content by any conventional technique for drying. Preferably, the drying of the sodium alaninate is carried out in two steps. In the first step, it is dried in a pre-evaporator at about 120 to about 270 mbar and about 90° C. (bath temperature) to a water content of about 5 to about 10%. In the second step, it is dried in a thin-layer evaporator at about 5 to about 25 mbar, preferably at about 12 to about 20 mbar, to a water content of at most about 1% by weight, preferably at most about 0.5% by weight.

The drying of the sodium alaninate in the thin-layer evaporator is carried out at about 140° to about 160° C. In a preferred embodiment of the present process, such drying is carried out at about 150° to about 160° C.

The residence time of the sodium alaninate in the thin-layer evaporator preferably is at most about 1 minute, particularly preferably at most 30 seconds.

The sodium alaninate obtained from the thin-layer evaporator is dissolved in a known manner in a solvent and the resulting solution is reacted directly with sodium L or DL-pantolactone to produce sodium D or DL-pantothenate. Suitable solvents include lower alkanols such as methanol and ethanol. Preferably, boiling methanol or ethanol is utilized in this reaction.

The following non-limiting Examples further illustrate the present invention. Unless otherwise stated, percentages (%) are percentages by weight and "parts" connote parts by weight. Temperatures are in degrees Celsius (°C.).

EXAMPLE 1

66 Parts of β-aminopropionitrile in 77 parts of water were saponified with 78 parts of aqueous (50% by weight) caustic soda in a stirring vessel. The saponification time was 4 hours and the temperature was about 98° to 100° C.

To neutralize the excess caustic soda, 11 parts of an aqueous solution of β-alanine (50% by weight) were added to the saponification solution.

The resulting solution was concentrated on a rotary evaporator at a partial vacuum of 120–270 mbar and at 90° C. to a residual water content of 7–10%.

The 118 parts of resulting sodium alaninate solution (with a solidifaction point of ca 80° C.) were then concentrated directly in a thin-layer evaporator to a residual water content of 1%. The thin-layer evaporator was operated at superheated steam temperatures of 150°–160° C. and a pressure of 5–25 mbar. The melt of 111 parts of sodium alaninate obtained as the sump product was dissolved directly in 300 parts of boiling methanol after removing the vacuum. The sodium alaninate in methanolic solution was reacted with 130 parts of L-pantolactone to give sodium D-pantothenate. The resulting compound was worked up and there resulted about 200 parts of sodium D-pantothenate. By worked up, it is meant that the D-pantothenate was crystallized from the methanolic solution, then centrifuged and dried in vacuum.

EXAMPLE 2

66 Parts of β-aminopropionitrile in 77 parts of water were saponified with 78 parts of aqueous (50% by weight) caustic soda in a stirring vessel. The saponification was carried out at a temperature of 130° C. and a pressure of 3 bar within 30 minutes.

To neutralize the excess caustic soda, 11 parts of an aqueous solution of 62 -alanine (50% by weight) were added to the saponification solution.

The resulting solution was concentrated on a rotary evaporator at a partial vacuum of 120-270 mbar and at 90° C. to a residual water content of 7-10%.

The 118 parts of resulting sodium alaninate solution (with a solidification point of ca 80° C.) were then concentrated directly in a thin-layer evaporator to a residual water content of 1%. The thin-layer evaporator was operated at superheated steam temperatures of 150°-160° C. and a pressure of 5-25 mbar. The melt of 111 parts of sodium alaninate obtained as the sump product was dissolved directly in 400 parts of boiling ethanol after removing the vacuum. The sodium alaninate in ethanolic solution was reacted with 130 parts of L-pantolacetone to give sodium D-pantothenate. The resulting compound was worked up as described in Example 1 and there resulted about 200 parts of sodium D-pantothenate.

EXAMPLE 3

In a manner similar to Example 1, β-aminopropionitrile can be saponified to form a sodium alaninate solution which can be neutralized and concentrated on a rotary evaporator and a thin-layer evaporator. The resulting melt of sodium alaninate can be dissolved in methanol and reacted with DL-pantolacetone to give sodium DL-pantothenate.

We claim:

1. In a process for producing crystalline sodium D-pantothenate from beta-aminopropionitrile, wherein beta-aminopropionitrile is saponified with aqueous caustic soda to produce a sodium alaninate solution, dry sodium alaninate is obtained from the solution, the dry sodium alaninate is dissolved in a lower alkanol solvent and reacted with pantolactone to give crystalline sodium D-pantothenate, the improvement comprising obtaining the dry sodium alaninate from said solution by:
   (a) drying said sodium alaninate solution in a pre-evaporator to produce sodium alaninate having a water content of about 5 to about 10% by weight; and
   (b) thereafter, further drying said sodium alaninate at a temperature of about 140° C. to about 60° C. in a thin-layer evaporator to a water content of at most about 1% by weight.

2. A process for producing dry sodium alaninate having a water content of at most about 1% by weight from an aqueous caustic soda solution of sodium alaninate, said dry sodium alaninate being suitable for use in producing crystalline sodium D-pantothenate, said process comprising:
   (a) drying said solution of sodium alaninate in a pre-evaporator to give sodium alaninate having a water content of about 5 to about 10% by weight; and
   (b) further drying said sodium alaninate at a temperature of about 140° C. to about 160° C. in a thin-layer evaporator to a water content of at most about 1% by weight.

3. In a process for producing crystalline sodium D-pantothenate from beta-aminopropionitrile wherein beta-aminopripionitrile is saponified with aqueous caustic soda to produce a sodium alaninate solution, dry sodium alaninate is obtained from the solution, the dry sodium alaninate is dissolved in a lower alkanol solvent and reacted with L-pantolactone to give crystalline sodium D-pantothenate, the improvement comprising obtaining dry sodium alaninate from said solution by:
   (a) drying said sodium alaninate solution in a rotary evaporator at about 120 mbar to about 270 mbar pressure at about 90° C. to give sodium alaninate having a water content of about 5 to about 10% by weight; and
   (b) further drying said sodium alaninate in a thin-layer evaporator at about 12 to about 20 mbar pressure at about 150° C. to about 160° C. to a water content of at most 1% by weight.

4. The process of claim 1 or 2 wherein the sodium alaninate is dried in the thin-layer evaporator at about 150° C. to about 160° C.

5. The process of claim 1 or 2 wherein the sodium alaninate is dried in the thin-layer evaporator for at most about 1 minute.

6. The process of claim 5 wherein the sodium alaninate is dried in the thin-layer evaporator for at most about 30 seconds.

7. The process of claim 1 or 3 wherein the solvent is boiling methanol or boiling ethanol.

8. The process of claim 1 wherein sodium L-pantolactone is reacted with said dissolved sodium alaninate to give crystalline sodium D-pantothenate.

9. The process of claims 1 or 2 wherein the pre-evaporator is a rotary evaporator.

10. The process of claims 1 or 2 wherein the drying in the pre-evaporator occurs at about 120 to about 270 mbar.

11. The process of claim 1 or 2 wherein the drying in the thin-layer evaporator occurs at about 5 to about 25 mbar.

12. The process of claim 11 wherein the sodium alaninate is dried in the thin-layer evaporator at about 12 to about 20 mbar pressure.

13. The process of claims 1 or 3 wherein the sodium alaninate is dried in the thin-layer evaporator to a water content of about 0.3 to about 1% by weight.

14. The process of claim 13 wherein the sodium alaninate is dried in the thin-layer evaporator to a water content of at most about 0.5% by weight.

* * * * *